(12) United States Patent
Shieh

(10) Patent No.: US 7,955,847 B2
(45) Date of Patent: Jun. 7, 2011

(54) METHOD FOR ENHANCING LEUKOCYTE IMMUNE FUNCTION

(75) Inventor: Chi-Chang K. Shieh, Tainan (TW)

(73) Assignee: Chi-Chang K. Shieh, Tainan (CN)

( * ) Notice: Subject to any disclaimer, the term of this patent is extended or adjusted under 35 U.S.C. 154(b) by 467 days.

(21) Appl. No.: 11/159,444

(22) Filed: Jun. 23, 2005

(65) Prior Publication Data

US 2007/0003527 A1    Jan. 4, 2007

(30) Foreign Application Priority Data

Jun. 23, 2004    (TW) ............................ 93118128 A

(51) Int. Cl.
C12N 5/00    (2006.01)
C12N 5/16    (2006.01)

(52) U.S. Cl. ........................................ 435/325; 435/340

(58) Field of Classification Search .................. 435/325, 435/340

See application file for complete search history.

(56) References Cited

OTHER PUBLICATIONS

Hjalmar Lagast, P. Daniel Lew, and Francis A. Waldvogel "Adenosine Triphosphate-dependent Calcium Pump in the Plasma Membrane of Guinea Pig and Human Neutrophils" J. Clin. Invest. vol. 73, Jan. 1984, 107-115.*
B. K. Rada et al. "Calcium signalling is altered in myeloid cells with a deficiency in NADPH oxidase activity" Clin Exp Immunol 2003;132:53-60.*
Answers.com "Chronic Granulomatous Disease" Accessed Jun. 26, 2007.*
Michael J. Chusid, M.D., and Peter A. Tomasulo, M.D. "Survival of Transfused Normal Granulocytes in a Patient With Chronic Granulomatous Disease" Pediatrics vol. 61 No. 4 Apr. 1978.*
C. P. Engelfriet et al. "Granulocyte T ransfusions" Vox Sang 2000;79:59-66.*
Roland Seifert, Rahel Burde and Günter Schultz "Activation of NADPH oxidase by purine and pyrimidine nucleotides involves G proteins and is potentiated by chemotactic peptides" Biochem. J. (1989) 259, 813-819.*

Karolyn P. Shatwell, Anthony W. Segal "Molecules in Focus NADPH Oxidase" Int. J. Biochem. Cell Biol. vol. 28, No. 11, pp. 1191-1195, 1996.*
Miklos Geiszt, Julia B. Szeberenyi, Krisztina Kaldi, and Erzsebet Ligeti "Role of Different Ca21 Sources in the Superoxide Production of Human Neutrophil Granulocytes" Free Radical Biology & Medicine, vol. 26, Nos. 9/10, pp. 1092-1099, 1999.*
Rae, J., Newburger, P.E., Dinauer, M.C., Noack, D., Hopkins, P.J. and Curnutte, J.T. ; 1998. X-Linked chronic granulomatous disease: mutations on the CYBB gene encoding the gp91-phox component of respiratiory-burst oxidase. Am. J. Hum. Genet. 62, 1320-1331.
Ellgaard, L., Molinari, M., and Helenius, A; 1999. Setting the standards: quality control in the secretory pathway. Science 286, 1882-1888.
Heyworth, P.G., Curnutte, J.T., Noack, D. and Cross, A.R.; 1997. Hematologically important mutations: X-linked chronic granulomatous disease-an update. Blood Cells Mol. Dis. 23, 443-450.
Roos, D., de-Boec-M., Kuribayashi. F. Meischl, C., Weeing, R.S., Segal, A.W., Ahlin, A., nemet, K., Hossle, J.P., Bernatowska-Matuszkiewicz, E. and Middleton-Price, H; 1996. Mutations in the X-linked and autosomal recessive forms of chronic granulomatous disease. [Revies][151 refs]. Blood 87, 1663-1681.
Lin, S.J., Huang, Y.F., Chen, J.Y., Heyworth, P.G., Noack, D., Wang, J.Y., Lin, C.Y., Chiang, B.L., Yang, C.M., Liu, C.C. and Shieh, C.C.; 2002. Molecular quality control machinery contributes to the leukocyte NADPH oxidase deficiency in chronic granulomatous disease. Biochim. Biophys. Acta 1586, 275-286.
Yeghen, T. and Devereuxs S.; 2001. Granulocyte transfusion: review. Vox Sang. 81, 87-92.
Yafang Huang and Chi-Chang Shieh; 2005. Rescuing mutant gp91phox from ER to restore the NADPH oxidase function in X-CGD cells with thapsigargin. Experimental Biology 2005, San Diego Convention Center, CA, USA.

* cited by examiner

*Primary Examiner* — Sandra E. Saucier
*Assistant Examiner* — Thane Underdahl
(74) *Attorney, Agent, or Firm* — Occhiuti Rohlicek & Tsao LLP

(57) ABSTRACT

The present invention provides a method for enhancing the immune function of leukocytes in a subject, which comprises the steps of: (a) isolating leukocytes from the subject; (b) treating the leukocytes obtained from step (a) with an inhibitor of the endoplasmic reticulum calcium ion pump; and (c) administrating the treated leukocytes obtained from step (b) back to the subject. A pharmaceutical composition for enhancing the immune function of leukocytes in a subject and a method for preparing said pharmaceutical composition are also provided.

15 Claims, 4 Drawing Sheets

METHOD FOR ENHANCING LEUKOCYTE IMMUNE FUNCTION

BACKGROUND OF THE INVENTION

1. Field of the Invention

The invention relates to a method for enhancing the immune function of leukocytes.

2. Description of the Related Art

Leukocytes play an important role in the immune system. They have the abilities to recognize and remove foreign substances so as to defend a subject from pathogens. Furthermore, leukocytes use various mechanisms to identify and remove abnormal molecules newly synthesized in leukocytes so as to avoid their harmful effects on cells (Ellgaard, L., Molinari, M., and Helenius, A; 1999. Setting the Standards: Quality Control in the Secretory Pathway. Science 286, 1882-1888).

Mutations or deficiencies in genes of leukocytes have been observed to lead to many congenital immune deficiencies or dysfunctions. Mutant leukocyte genes may encode erroneous proteins which exhibit abnormal leukocyte functions and lead to immune deficiencies or dysfunctions. Generally, products of mutant genes are often detected at the early stage of the biosynthetic process of proteins. The quality control mechanism in cells will be triggered wherein premature proteins translated by mutant genes are degraded by enzymes and removed from cells. Previous investigations have revealed that the degradation of premature proteins may occur at the transcription or translation stage (Ellgaard et al., 1999, Supra). For complex proteins, mutant peptides will be retained in the endoplasmic reticulum by molecular chaperons which lead to degradation pathways in the cytoplasm. This molecular quality control mechanism can avoid the wasteful production of useless or even harmful mutant proteins from valuable resources in cells which harbor mutant genes. On the other hand, since the mechanism is initiated by the mutations, mutant proteins which still exhibit some functions are removed as well as the useless or harmful molecules. As for X-linked or homozygous genes, their removal may cause severe genetic diseases.

For example, chronic granulomatous disease (CGD) is a hereditary immunodeficiency caused by deficiencies in reduced nicotinamide adenine dinucleotide phosphate (NADPH) oxidase of phagocyte. NADPH oxidase is composed of flavocytochrome $b_{558}$, formed by cell membrane-bound gp91-phox and p22-phox, and the cytoplasmic proteins p40-phox, p47-phox and p67-phox. Leukocyte NADPH oxidase requires non-peptide cofactors of heme (the prosthetic group) and cofactor flavin adenine dinucleotide (FAD) to from a functional complex. If mutations occur at domains of the enzyme which bind to these cofactors, or at other domains, the enzyme will fail to function in the catalytic production of reactive oxygen species (ROS), including superoxide and hydrogen peroxide. Young patients may hence suffer from recurrent microbial infections. (See Rae, J., Newburger, P. E., Dinauer, M. C., Noack, D., Hopkins, P. J. and Curnutte, J. T.; 1995 X-Linked Chronic Granulomatous Disease: Mutations on the CYBB Gene Encoding the gp91-phox Component of Respiratory-Burst Oxidase. Am J. Hum. Genet. 62, 1320-1331) Many publications have disclosed that mutations with respect to the genes gp91-, p22-, p67-, and p47-phox will cause chronic granulomatous diseases (Heyworth, P. G., curnutte, J. T., Noack, D. and Cross, A. R.; 1997. Hematologically Important Mutations: X-linked Chronic Granulomatous Disease-an Update. Blood Cells Mol. Dis. 23, 443-450; Roos, D., de Boer, M., Kuribayashi. F. Meischl, C., Weeing, R. S., Segal, A. W., Ahlin, A., nemet, K., Hossle, J. P., Bernatowska-Matuszkiewicz, E. and Middleton-Price, H; 1996. Mutations in the X-linked and Autosomal Recessive Forms of Chronic Granulomatous Disease. Blood 87, 1663-1681; Noack, D., Rae, J., Cross, A. R., Ellis, B. A., Newburger, P. E., Curnutte, J. T. and Heyworth, P. G.; 2001. Autosomal Recessive Chronic Granulomatous Disease Caused by Deficiencies in NCF-1, the Gene Encoding the Phagocyte p47-phox: Mutations not Arising in the NCF-1 Pseodogenes. Blood 97, 305-311). X-linked chronic granulomatous disease (X91 CGD) is further reported. Molecular quality control mechanism in the nucleus or endoplasmic reticulum monitors the production of proteins synthesis destined for plasma membrane and endocytic organelles (Lin, S. J., Huang, Y. F., Chen, J. Y., Heyworth, P. G., Noack, D., Wang, J. Y., Lin, C. Y., Chiang, B. L., Yang, C. M., Liu, C. C. and Shieh, C. C.; 2002. Molecular quality control machinery contributes to the leukocyte NADPH oxidase deficiency in chronic granulomatous disease. Biochim. Biophys. Acta 1586, 275-286).

Current methods for treating deficient leukocyte function include bone marrow transplantation, gene therapy and cytokine therapy. Although bone marrow transplantation has been well developed for several years, its application is still restricted because bone marrow cell donors with a matching genotype are not available in many cases. Furthermore, recipients are at the risk of graft versus host disease (GvHD) and being infected by donors. Gene therapy involves the introduction of a foreign DNA sequences that replace the defective DNA structure of cells. However, this treatment is still hampered by the complications including malignant transformation and septic shock. Due to safety concerns, the application of gene therapy is on hold. Currently, cytokine therapy is only applied to a few diseases. Such therapies often fail to sufficiently restore the function of cells expressing mutant proteins and are very costly. In addition, because the deficient or mutant genes are often expressed only in specific sites, such as in blood cells, severe side-effects may occur when the drugs are administered systemically.

Therefore, a method for enhancing the immune function of leukocytes bearing mutant proteins without severe side effects is needed in the art.

SUMMARY OF THE INVENTION

One object of the invention is to provide a method for enhancing the immune function of leukocytes in a subject, which comprises the steps of:
(a) isolating leukocytes from the subject;
(b) treating the leukocytes obtained from step (a) with an inhibitor of the endoplasmic reticulum calcium ion pump; and
(c) administrating the leukocytes treated in step (b) back to the subject.

Preferably, step (b) comprises co-treating the leukocytes obtained from step (a) with a non-peptide cofactor and the inhibitor of the endoplasmic reticulum calcium ion pump.

In one preferred embodiment of the invention, the method is for treating chronic granulomatous disease.

Another object of the invention is to provide a pharmaceutical composition for enhancing the immune function of leukocytes in a subject comprising leukocytes treated with an inhibitor of the endoplasmic reticulum calcium ion pump; wherein the leukocytes are derived from the subject.

Yet another object of the invention is to provide a method for preparing the pharmaceutical composition of the invention, which comprises the steps of:

(a) isolating leukocytes from the subject; and
(b) treating the leukocytes obtained from step (a) with an inhibitor of the endoplasmic reticulum calcium ion pump.

DETAILED DESCRIPTION OF THE INVENTION

Figure 1:
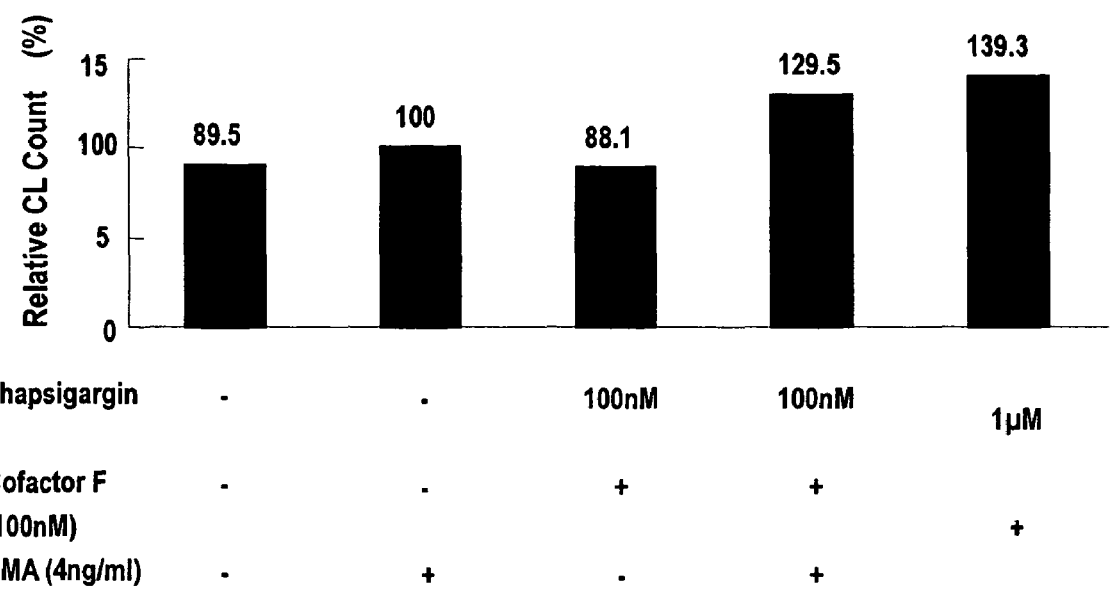
FIG. 1 illustrates the enhancement of NADPH oxidase activity after the treatments with cofactor FAD and/or thapsigargin.

The invention provides a method for enhancing the immune function of leukocytes in a subject, which comprises the steps of:
(a) isolating leukocytes from the subject;
(b) treating the leukocytes obtained from step (a) with an inhibitor of the endoplasmic reticulum calcium ion pump; and
(c) administrating the leukocytes treated in step (b) back to the subject.

The invention also provides a pharmaceutical composition for enhancing the immune function of leukocytes in a subject comprising leukocytes treated with an inhibitor of the endoplasmic reticulum calcium ion pump; wherein the leukocytes are derived from the subject.

One characteristic of the invention is to specifically repair deficient or dysfunctional leukocytes in the immune system, in contrast to the conventional bone marrow transplantation, gene therapy and cytokine therapy, which treat the patient systemically. The method according to the invention completely overcomes the safety concern, application restriction, severe side effects, and poor efficacy of the conventional methods. According to the invention, the leukocytes derived from the subject to be treated are treated with an inhibitor of the endoplasmic reticulum calcium ion pump. After treating the subject according to the invention, the immune response is improved due to the restoration of the immune function of the treated leukocytes. As a result, the method of the invention is applicable to the treatment of immune deficient or dysfunctional diseases.

Another characteristic of the invention is to enhance the immune activity of leukocytes by controlling the calcium ion concentration of in the endoplasmic reticulum. The calcium ion in the endoplasmic reticulum is an important second messenger that down-regulates several enzymes and/or proteins for important cell signal transductions. Molecular chaperons in the endoplasmic reticulum related to the protein synthesis in cells are also controlled by the calcium ion in the endoplasmic reticulum. The calcium ion concentration in the endoplasmic reticulum is regulated by the endoplasmic reticulum calcium ion pump. The calcium ions are transported from the cytoplasm into the endoplasmic reticulum by the calcium ion pump to maintain a specific concentration in cells. After receiving the signals, chaperons turn on the quality control mechanism in the cells, which retains mutant proteins on the molecular chaperons instead of transporting them to the target sites such as cell membrane. According to the invention, controlling the endoplasmic reticulum calcium ion pump may lower the calcium ion concentration in the endoplasmic reticulum and then regulate the activity of molecular chaperons. When an inhibitor of the endoplasmic reticulum calcium ion pump is used, the calcium ion concentration in the endoplasmic reticulum is lowered and the molecular chaperons will not bind to mutant proteins that still retain some functions. As a result, the mutant proteins that still retain some functions are successfully transported to the target site and the immune deficiency due to the lack of proteins is thus repaired. The immune activity of deficient or dysfunctional leukocytes is raised thereby. In another aspect, for the deficiency or dysfunction of leukocytes unrelated to gene mutations, the method according to the invention can also rapidly enhance the immune activity of leukocytes. When the calcium ion concentration in the endoplasmic reticulum is lowered, proteins newly synthesized in cells can rapidly pass the quality control mechanism, such as molecular chaperons, and therefore can be transported to the target sites more efficiently. As such, the immune activity of leukocytes is enhanced.

The inhibitor of the endoplasmic reticulum calcium ion pump according to the invention has an inhibitory effect on the endoplasmic reticulum calcium ion ATPase. Preferably, the inhibitor is thapsigargin. Thapsigargin, the most broadly used inhibitor of the endoplasmic reticulum calcium ion ATPase is usually used in researches concerning calcium ion signal transduction mechanism in cells. Other inhibitors of the endoplasmic reticulum calcium ion pump are also applicable to the invention for lowering the calcium ion concentration in the endoplasmic reticulum and for further regulating the binding of the molecular chaperon on the endoplasmic reticulum membrane to mutant proteins.

The method according to the invention can be broadly used to treat immune deficiency or dysfunction related or unrelated to gene mutations, in particular for treating diseases implicated with high calcium ion concentration in the endoplasmic reticulum, such as bacteriemia, severe infections, phagocytic leukocyte dysfunction, or lymphocyte dysfunction, such as chronic granulomatous disease.

The isolation of leukocytes from a subject in step (a) of the method of the invention can be performed in a manner well known to persons of ordinary skill in the art. For instance, the buffy coats of blood samples form the subject are collected, and the leukocytes thereof are adhered onto a nylon fiber and collected. A common technique is first isolating blood cells from blood samples by centrifugation and then treating the blood cells with a sedimenting agent for separating leukocytes from red blood cells. Commonly used sedimenting agents are selected from the group consisting of dextran, hydroxyethyl starch (HES), low-molecular-weight hydroxyethyl starch (also known as pentastarch), and modified gelatin derivatives such as plasmagel. Hydroxyethyl starch and petastarch are often used in place of dextran for collecting leukocytes (Yeghen, T. and Devereuxs S.; 2001. Granulocyte transfusion: review. Vox Sang. 81, 87-92). In addition, granulocyte-colony stimulating factors (G-CSF) and corticosteroids can be used to facilitate the collection of leukocytes as they are known to enhance the release of leukocytes from the bone marrow and to decrease the efflux of circulating lymphocytes from the blood. For instance, a single dose of dexamethasone, 8 mg p.o., 12 to 24 hours before apheresis, provides good results with little side-effects.

The treatment of the leukocytes obtained from step (a) with an inhibitor of the endoplasmic reticulum calcium ion pump may vary along with the species of the inhibitor, which depends on the property, safety and potency of the inhibitor. For example, treatment with thapsigargin is advantageously performed in a range from 50 nm to 10 M; preferably, 100 nm.

In one preferred embodiment of the method according to the invention, step (b) comprises co-treating the leukocytes obtained from step (a) with the inhibitor of the endoplasmic reticulum calcium ion pump and a non-peptide cofactor. The leukocytes so co-treated exhibit a stronger immune function. The non-peptide cofactor is essential for several enzymes/proteins to exhibit their biochemical activity. The non-peptide cofactor assembles a functional complex with peptide parts of the enzymes/proteins. In some cases, the non-peptide cofactor itself participates in the biochemical reaction of the enzymes/proteins, e.g., functions as a substrate for the reaction. For example, NADPH oxidase requires the non-peptide cofactors of heme and flavin adenine dinucleotide to assemble a functional complex. When an oxidation involving NADPH is carried out, the addition of NADPH enhances the efficiency. Preferably, the non-peptide cofactor is selected from the group consisting of FAD, FADH, $NAD^+$, NADH, $NADP^+$, NADPH, AMP, ADP, ATP, vitamins, metal ions, FMN, coenzyme A, coenzyme Q, folic acid, nicotinic acid and cytochrome.

The invention also provides a pharmaceutical composition for enhancing the immune function of leukocytes in a subject comprising leukocytes treated with an inhibitor of the endoplasmic reticulum calcium ion pump; wherein the leukocytes are derived from the subject. Preferably, the leukocytes are further treated with a non-peptide cofactor.

In one preferred embodiment of the invention, the method and the pharmaceutical composition of the invention are used to treat chronic granulomatous disease.

The present invention also provides a method for preparing the pharmaceutical composition of the invention, which comprises the steps of:
 (a) isolating leukocytes from the subject; and
 (b) treating the leukocytes obtained from step (a) with an inhibitor of the endoplasmic reticulum calcium ion pump.

The following examples are given for the purpose of illustration only, and are not intended to limit the scope of the present invention.

Example 1

Effects of Thapsigargin and Cofactor FAD in Restoring the Activity of Granulocyte NADPH Oxidase Blood samples with EDTA were obtained from patients with X91-chronic granulomatous disease. The samples were water bathed at 37° C. in a lysate buffer containing ammonium chloride, sodium carbonate and EDTA for several minutes to lyze residual red blood cells. The samples were then added with a suspension buffer containing globulin and EDTA to wash and remove the residual lysate buffer. The leukocytes were collected by centrifugation and counted.

Total leukocytes were maintained in RPMI 1640 medium supplemented with 10% heat-inactivated FBS at 37° C. under a humidified atmosphere (5% $CO_2$+95% air). The leukocytes were seeded at a density of 3 to $5\times10^5$/ml and grown for 2 hrs in the presence or absence of 100 nM cofactor FAD and/or thapsigargin (100 nM or 1 μM). The cells were then cultured in 10% RPMI to recover for 1 hr prior to the following experiments.

The leukocyts were suspended in a suspension buffer with a concentration of $8\times10^5$ granulocytes/ml. Phorbol myristate-13-acetate (PMA) was added, 4 ng/ml, to activate the NADPH oxidase. The superoxide production was determined by luminol-enhanced chemiluminescence in the chamber of the Chemiluminescence Analyzer System (Tohoku™ Electronic Inc., Japan). The reaction concentration of luminol was $2\times10^{-5}$ M.

The NADPH oxidase activity was shown in FIG. 1. As can be seen, the activity of granulocytes isolated from the X91-CGD patient which were treated with cofactor FAD and thapsigargin in superoxide production is enhanced by 30% than that of untreated cells.

Example 2

Figure 2:
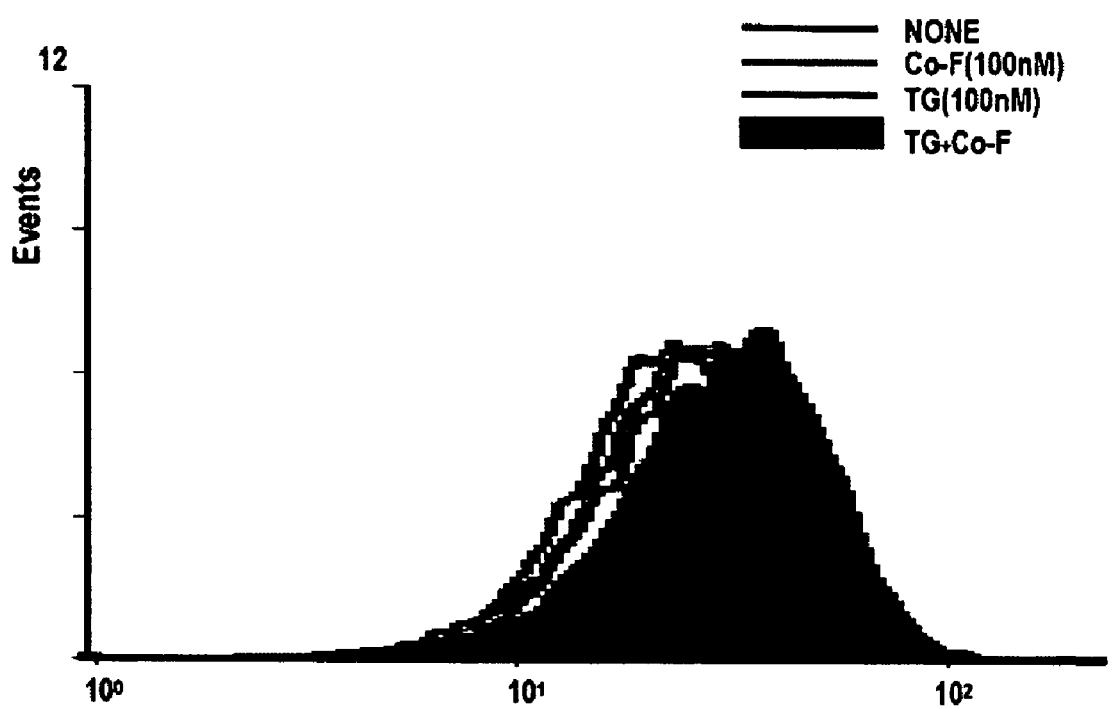
FIG. 2 illustrates the enhancement of cell surface NADPH oxidase after the treatments with cofator FAD and/or thapsigargin.

Effects of Thapsigargin and Cofactor FAD in Enhancing the Activity of NADPH Oxidase on Leukocyte Surface To test whether the treatment with thapsigargin or cofactor FAD alone or in combination has effects on the cell surface expression of leukocyte NADPH oxidase, the cell surface expressions of cytochrome $b_{558}$ in leukocytes with or without desired treatment were assayed. Leukocytes were prepared as illustrated in Example 1. The leukocytes, at the concentration of $5\times10^5$ cells/ml, were incubated with anticytochrome $b_{558}$ monoclonal antibody (7D5) at 4° C. for 30 min, followed by incubation with FITC-labeled goat anti-mouse IgG for 40 min. The treated leukocytes were analyzed with flow cytometry and shown in FIG. 2.

As can be seen, while the combined treatment significantly increased the cell surface NADPH oxidase expression, treatments with thapsigargin or cofactor FAD alone slightly enhanced the expression.

Example 3

Effects of Thapsigargin and Cofactor FAD on the Bactericidal Activity of Granulocytes The effects of treatment with thapsigargin or cofactor FAD alone or in combination on the bactericidal activity of granulocytes were assayed. The preparation of leukocytes was as illustrated in Example 1.

Treated leukocytes, at the concentration of $1\times10^6$ cells/ml, were incubated with 10 ml *S. aureus* ($1\times10^6$ CFU) and 20 ml serum isolated from the same patient at 37° C. for 90 min. After 90 min, the samples were treated with 10 ml Lysostaphin (1 U) for 10 min, and the cells were washed with PBS for three times. The cells were re-suspended with 400 ml sterile water and vortexed to disrupt the cells. The lysate was then plated on 5% TSA plates. After incubation at 37° C. overnight, the colonies were counted and the results are shown in FIG. 3.

Figure 3:
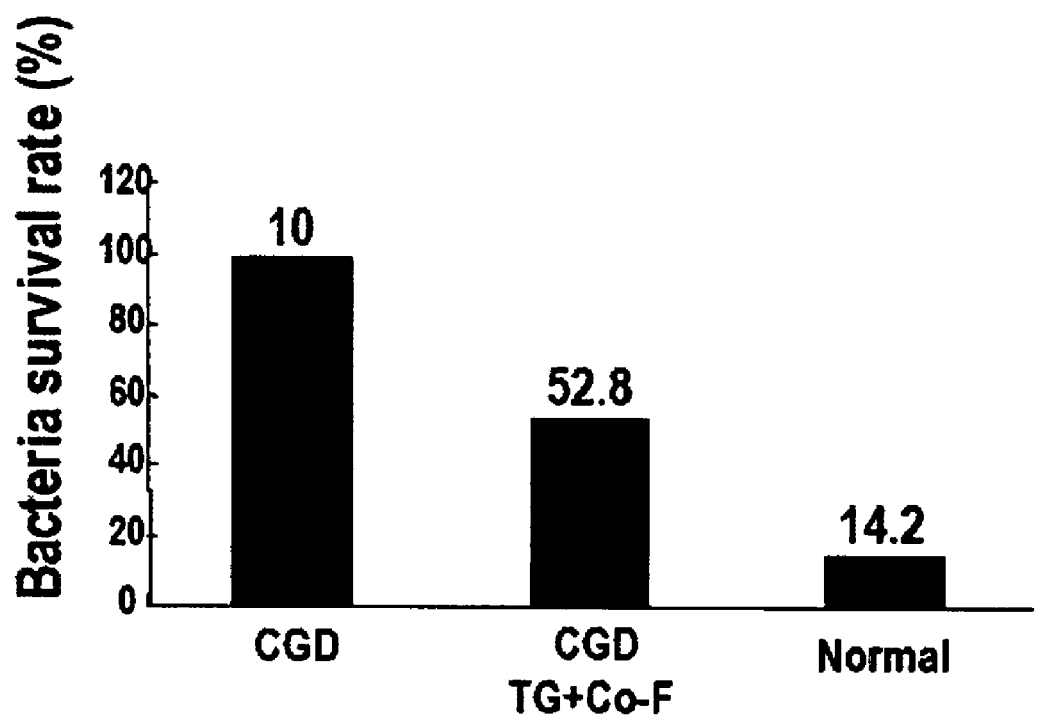
FIG. 3 illustrates the bactericidal activity of granulocytes isolated from the X91-CGD patient treated with/without cofactor F combined with thapsigargin.

As can be seen from FIG. 3, survival rate of bacteria cultured with the leukocytes treated in accordance with the invention is lowered to 52.83% as compared with survival rare of observed with patients with chronic granulomatous disease. It shows that the bactericidal activity of granulocytes was enhanced enormously after thapsigargin and cofactor FAD treatments.

Figure 4A:
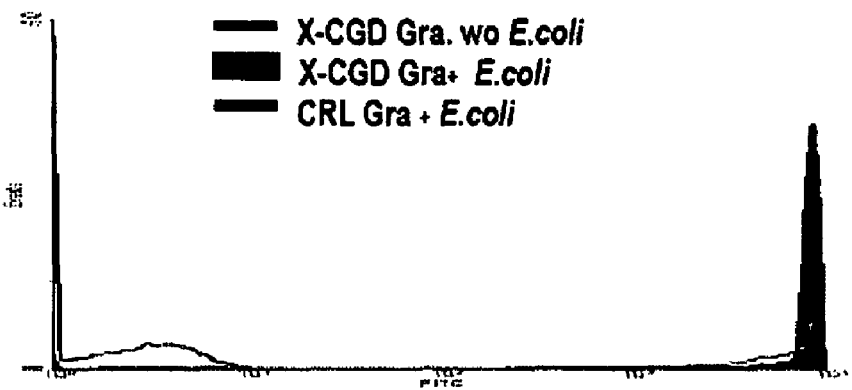
FIG. 4 illustrates the phagocytic activity of granulocytes isolated from the X91-CGD patient treated with/without cofactor F combined with thapsigargin. A: without treatment. B: with treatment.
Figure 4B:
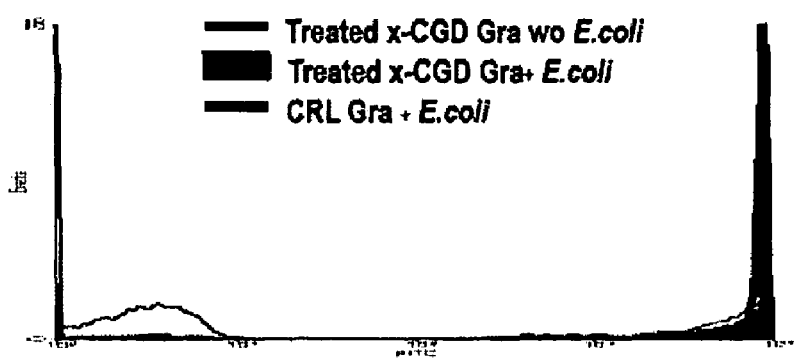

To confirm that the above reduced bacterial survival rate is due to the increase in the bactericidal activity rather than the change in the efficiency of phagocytosis, the effects of thapsigargin and cofactor FAD on phagocytes were assayed and the results are shown in FIG. 4.

As shown in FIG. 4, treated and untreated leukocytes showed no difference regarding bacterial phagocytosis. Accordingly, the reduced bacterial survival rate is proven to relate to an enhanced bactericidal activity.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A method for treating chronic granulomatous disease in a subject, which comprises the steps of:
   (a) isolating leukocytes from the subject having chronic granulomatous disease;
   (b) treating the leukocytes obtained from step (a) with an effective amount of an inhibitor of the endoplasmic reticulum calcium ion pump to increase the bactericidal activity of the leukocytes, and
   (c) administrating the leukocytes treated in step (b) back to the subject such that said treated leukocytes have an increase in bactericidal activity.

2. The method according to claim 1, which is for treating a subject having chronic granulomatous disease with symptoms of bacteriemia or severe infections.

3. The method according to claim 1, wherein the leukocytes is obtained from step (a) by treating a blood sample with a sedimenting agent for separating the leukocytes from the red blood cells.

4. The method according to claim 3, wherein the sedimenting agent is selected from the group consisting of dextran, hydroxyethyl starch (HES), low-molecular-weight hydroxyethyl starch, and modified gelatin derivatives.

5. The method according to claim 4, wherein the sedimenting agent is hydroxyethyl starch or low-molecular-weight hydroxyethyl starch.

6. The method according to claim 1, wherein prior to step (a), the subject is treated with a granulocyte-colony stimulating factor (G-CSF) or a corticosteroid.

7. The method according to claim 6, wherein the corticosteroid is dexamethasone.

8. The method according to claim 1, wherein the inhibitor of the endoplasmic reticulum calcium ion pump is thapsigargin.

9. The method according to claim 1 wherein step (b) comprises co-treating the leukocytes obtained from step (a) with the inhibitor of endoplasmic reticulum calcium ion pump and a non-peptide cofactor selection from the group consisting of FADH, FAD, NAD+, NADH, NADP+, NADPH, AMP, ADP, ATP, vitamins, metal ions, coenzyme A, coenzyme Q, folic acid, nicotinic acid, and cytochrome.

10. The method according to claim 9, wherein the non-peptide cofactor is ATP.

11. The method according to claim 9, wherein the non-peptide cofactor is a metal ion.

12. The method according to claim 9, wherein the non-peptide cofactor is FAD.

13. The method according to claim 1, wherein the leukocytes before treatment are NADPH oxidase deficient.

14. The method according to claim 1, wherein the leukocytes obtained from step (a) is treated with 50 nm to 10 M thapsigargin.

15. The method according to claim 14, wherein the leukocytes obtained from step (a) is treated with 100 nm thapsigargin.

* * * * *

UNITED STATES PATENT AND TRADEMARK OFFICE
CERTIFICATE OF CORRECTION

| | | |
|---|---|---|
| PATENT NO. | : 7,955,847 B2 | |
| APPLICATION NO. | : 11/159444 | |
| DATED | : June 7, 2011 | |
| INVENTOR(S) | : Chi-Chang K. Shieh | |

It is certified that error appears in the above-identified patent and that said Letters Patent is hereby corrected as shown below:

Please change the assignee address on page 1, item (73) from Tainan (CN) to read:

Tainan (TW)

Signed and Sealed this
Twenty-third Day of August, 2011

David J. Kappos
*Director of the United States Patent and Trademark Office*